United States Patent [19]
Akselrod et al.

[11] Patent Number: 5,135,000
[45] Date of Patent: Aug. 4, 1992

[54] METHOD OF MEASURING REGIONAL TISSUE BLOOD FLOW

[75] Inventors: Solange Akselrod, Givat Shmuel; Victor Mor-Avi, Kiryat Ono; Daniel David, Raanana, all of Israel

[73] Assignee: Raizot University Authority for Applied Research & Industrial Development Ltd., Tel-Aviv, Israel

[21] Appl. No.: 761,147

[22] Filed: Sep. 17, 1991

[30] Foreign Application Priority Data

Sep. 19, 1990 [IL] Israel .......................................... 95743

[51] Int. Cl.$^5$ ................................................ A61B 8/00
[52] U.S. Cl. ............................ 128/662.02; 128/660.05
[58] Field of Search ....................... 128/660.05, 661.08, 128/661.04, 662.05, 662.02

[56] References Cited

U.S. PATENT DOCUMENTS

| | | | |
|---|---|---|---|
| 4,265,251 | 5/1981 | Tickner | 128/662.02 |
| 4,630,612 | 12/1986 | Uchida et al. | 128/660.05 |
| 5,040,537 | 8/1991 | Katakura | 128/662.02 |

*Primary Examiner*—Francis Jaworski
*Assistant Examiner*—George Manuel
*Attorney, Agent, or Firm*—Benjamin J. Barish

[57] ABSTRACT

A method of measuring blood flow through tissue in a region of interest including the steps: injecting an ultrasonic tracer into the blood upstream of the region of interest and also upstream of a specified reference region; utilizing the tracer-produced echo intensity function to compute: (i) the mean transit time of the tracer through the region of interest; and (ii) the blood volume within the region of interest; and dividing the results of computation (ii) by computation (i) to produce a quantitative measurement of the blood flow through the tissue in the region of interest.

10 Claims, 6 Drawing Sheets

FIG.3a
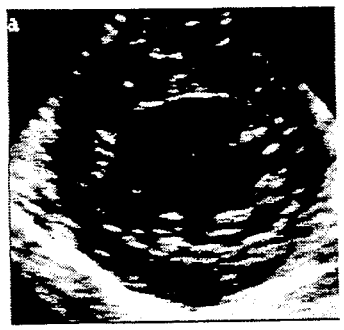
FIG.3b
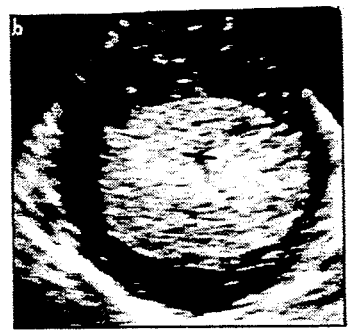
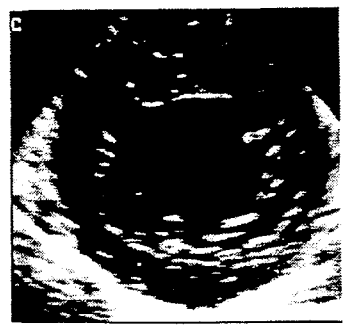
FIG.3c
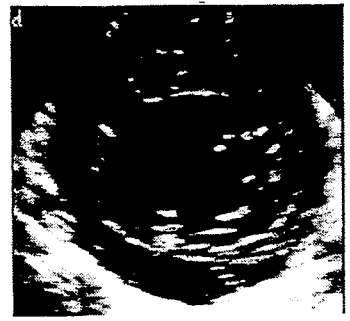
FIG.3d

METHOD OF MEASURING REGIONAL TISSUE BLOOD FLOW

The present invention relates to a method of measuring blood flow through tissue in a region of interest, and particularly blood flow through the heart muscle tissue.

GENERAL BACKGROUND

Coronary heart disease is one of the most substantial threats to human life in the modern society. Hence, the importance of fast reliable non-invasive methods for the early detection of coronary heart disease may hardly be overestimated. One of the important parameters in the assessment of the physiological impact of coronary disease is the blood supply to various regions of the heart muscle. Reduced blood flow in the coronary capillary bed leads to insufficient blood supply and causes impairment of myocardial function. To date, there is no reliable method for the quantitative assessment of myocardial tissue blood flow, either invasive or non-invasive. Most of the techniques in current use provide information only on relative changes in regional myocardial blood flow, and none is sufficiently sensitive and accurate to supply a reliable absolute quantitative measurement in vivo. Moreover, the use of most of the known methods in humans is limited due to their invasive nature and high cost.

One of the recent developments promising to satisfy the clinical need for direct assessment of regional myocardial blood flow is associated with the use of contrast materials in ultrasonic imaging of the heart. A sonicated human Albumin solution was recently shown to be a nontoxic carrier of stable reproducible microscopic air bubbles comparable in size with the red blood cells (about 5 $\mu$m in diameter), and therefore suitable for echocardiographic enhancement in humans. Using this material and other contrast enhancing solutions, the indirect qualitative assessment of myocardial tissue blood flow has been achieved. Visual examination of the differences in time dependence of the ultrasonic intensity reflected from various regions of the myocardium, following intracoronary or aortic root injection of the contrast solution, allowed the differentiation between underperfused and normally perfused myocardial tissue. Regions of myocardial tissue suffering from insufficient blood supply, are characterized by considerably lower contrast level and longer contrast clearance times, as compared with the normally supplied regions of the heart.

There have been several suggestions for providing quantitative markers related to regional blood flow, such as the time of peak contrast, the area under contrast appearance and washout curves, etc. However, insofar as we are aware, none provide a direct quantitative measurement of regional blood flow.

OBJECT AND SUMMARY OF THE INVENTION

The object of the present invention is to provide a method of quantitatively measuring blood flow through tissue in a region of interest, and particularly the myocardial tissue blood flow.

According to the present invention, there is provided a method for measuring blood flow through the tissue in a region of interest, comprising:
(a) injecting an ultrasonic tracer substance into the blood upstream of the region of interest and also upstream of a specified reference region;
(b) subjecting the region of interest and the specified reference region to two-dimensional ultrasonic imaging;
(c) subjecting the acquired images to digital path-dependent attenuation recompensation for propagation effects, varying with time due to the contrast transit, such as attenuation due to scattering and absorption, so as to produce regional video intensity independent of tracer concentration in the surrounding regions, in particular those more proximal to the transducer;
(d) simultaneously detecting the echo intensity at the region of interest and the reference region at the same phase of a series of successive heartbeats, to produce echo intensity values as a function of time for the region of interest and for the reference region;
(e) measuring the mean background value in each region before the injection, and subtracting the mean background values from the detected echo intensity values at both regions to produce a measurement of the tracer-produced echo intensity functions;
(f) utilizing said latter measurement (of the tracer-produced echo intensity functions) to compute: (i) the mean transit time of the tracer through the region of interest; and (ii) the blood volume within the region of interest;
(g) dividing the results of (f) (ii) by (f) (i) to produce a quantitative measurement of the blood flow through the tissue in the region of interest.

According to further features in the embodiment of the invention described below, the mean transit time of the tracer through the region of interest in step (e) is computed by:
(a) transforming the tracer-produced echo intensity functions in each region from the time domain to the frequency domain to produce a frequency domain intensity function for each region;
(b) dividing the frequency domain intensity function in the region of interest by the frequency domain intensity function in the reference region to produce the transfer function of the tissue in the region of interest;
(c) transforming the transfer function of the region of interest from the frequency domain to the time domain to produce the response function of the tissue in the region of interest;
(d) and utilizing the latter response function to compute the mean transit time of the tracer through the tissue in the region of interest.

According to still further features in the described embodiment, the blood volume within the region of interest is computed by:
(a) integrating with respect to time the tracer-produced echo intensity functions in the region of interest and in the reference region; and
(b) dividing the former by the latter to produce a measurement of the fractional blood volume within the tissue in the region of interest, which when divided by the mean transit time, produces a measurement of the blood flow through the tissue per unit mass of the tissue.

The tracer substance is a solution containing microscopic particles, about the size of the red blood cells, capable of enhancing the intensity of the ultrasonic reflection.

The present invention is based on a theoretical model, briefly described below, which links the intensity of the ultrasonic reflections with the physics of the blood flow in myocardial tissue and thus allows a quantitative evaluation of regional blood flow in the heart muscle tissue. Since the successful enhancement of the left heart chambers by peripheral intravenous injection of contrast material has been recently achieved, the echocardiographic imaging may permit a non-invasive assessment of regional tissue blood flow based on the above described method.

BRIEF DESCRIPTION OF THE DRAWINGS

The invention is more particularly described, by way of example only, with reference to the accompanying drawings, wherein:

FIGS. 3a–3d illustrate four ultrasonic images of a short axis view of a heart obtained in practicing the method in the example described below;

THEORETICAL DISCUSSION

Figure 1:
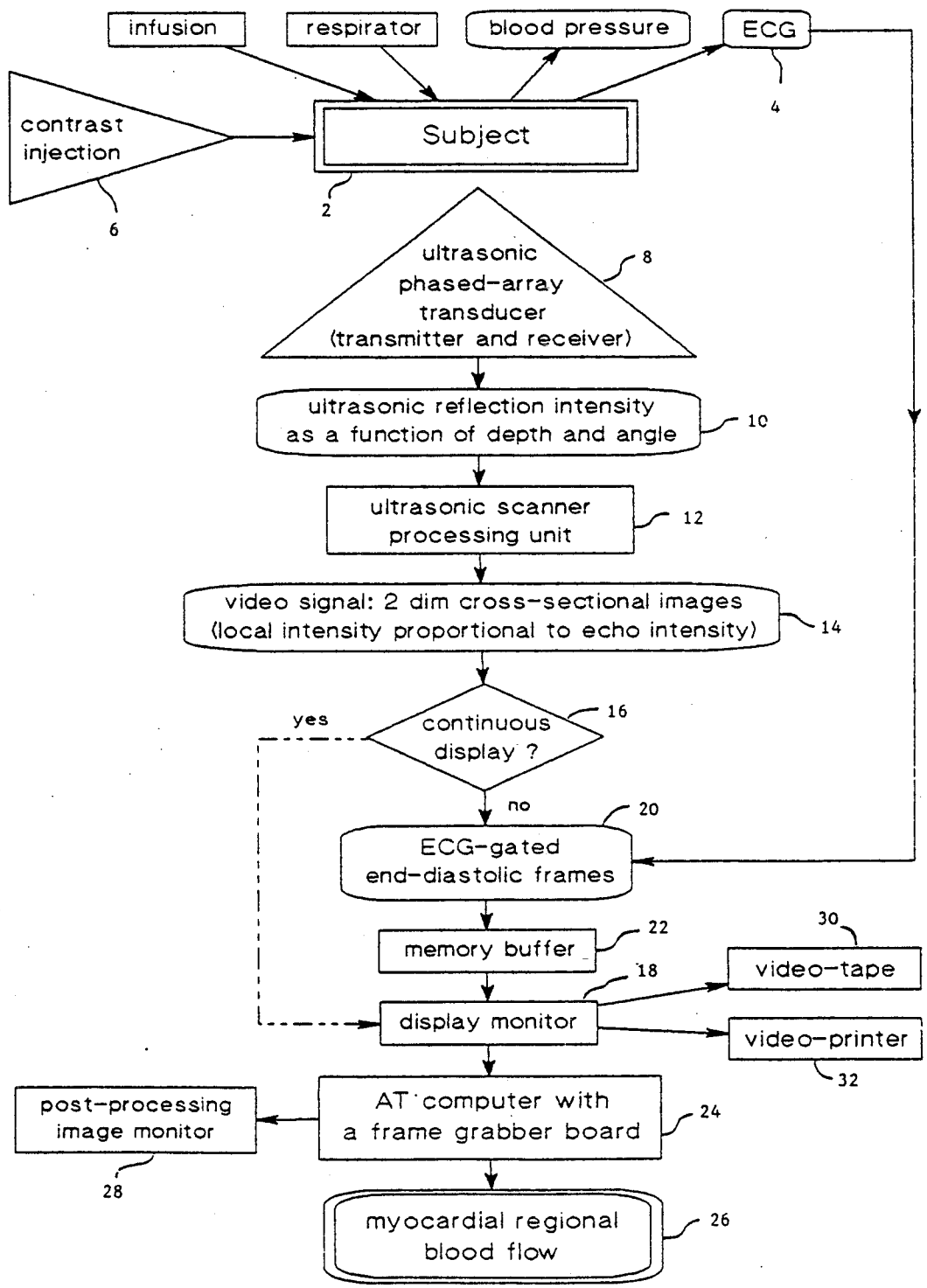
FIG. 1 diagrammatically illustrates one method for practicing the invention as more particularly described below.
Figure 2:
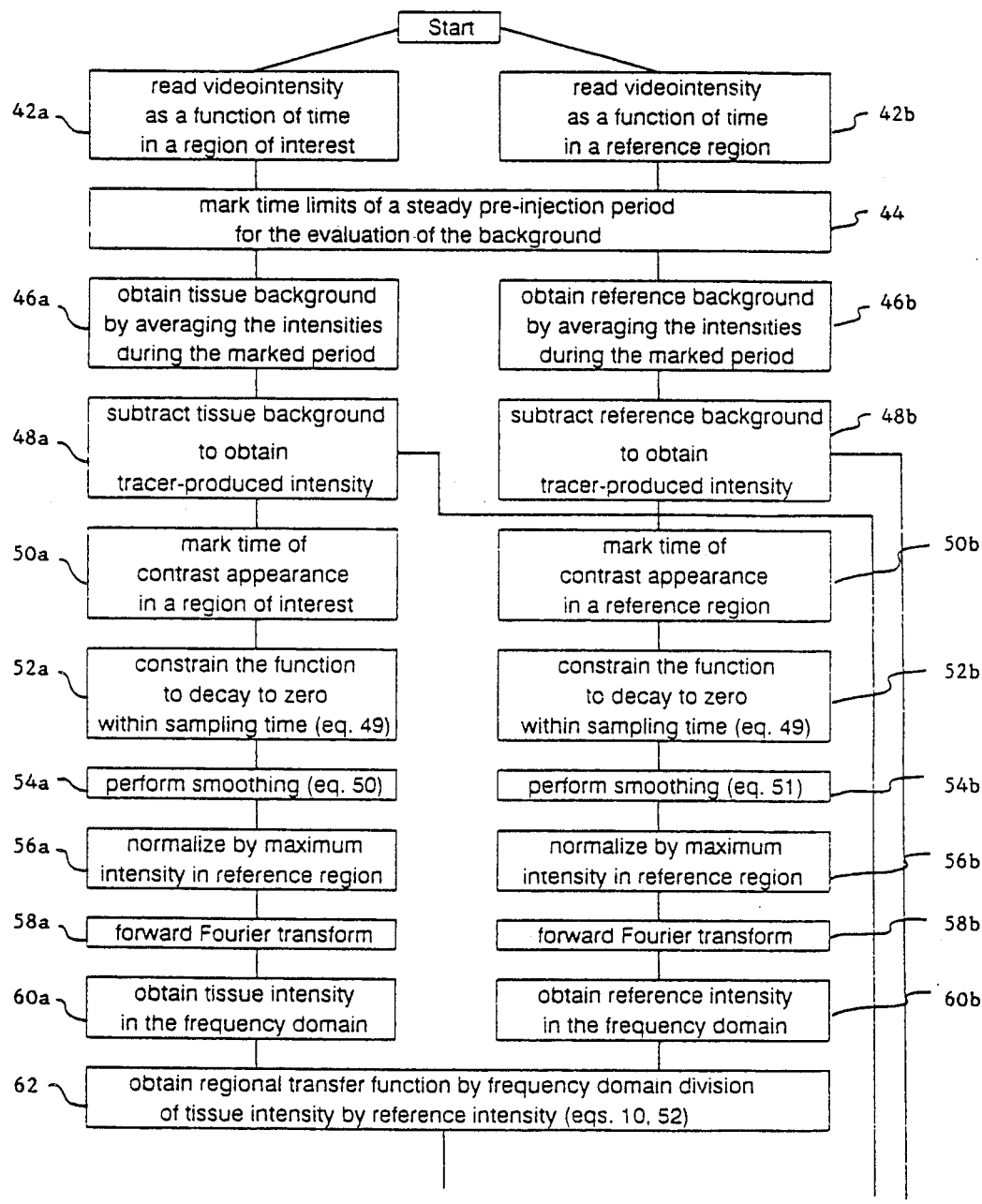
FIGS. 2 and 2a, taken together, constitute a flow chart illustrating the operations performed in practicing the invention according to the example described below.
Figure 2A:
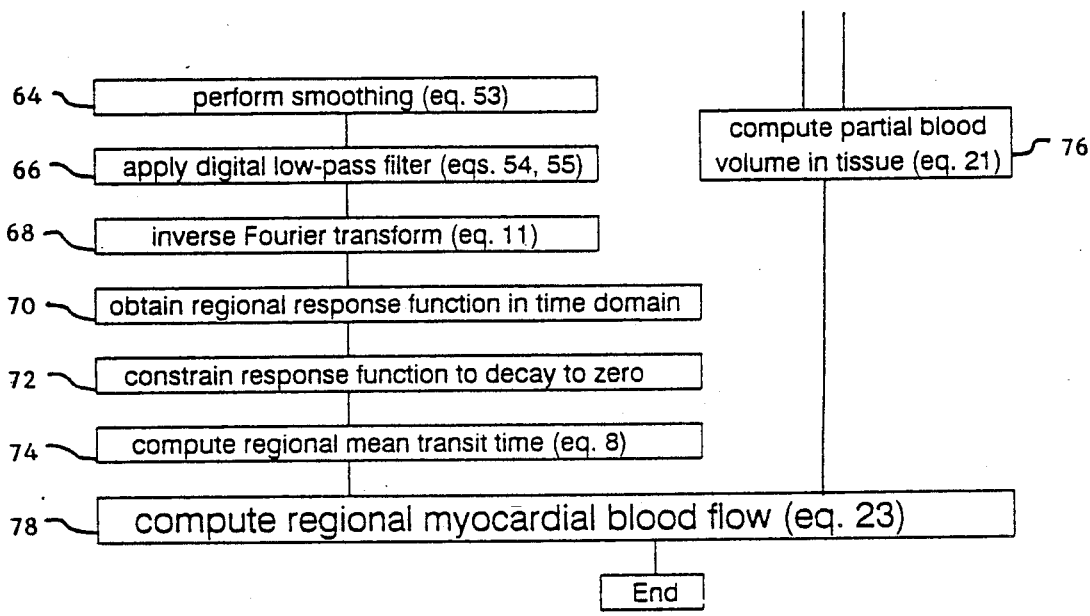
Figure 4A:
FIGS. 4a–4d illustrate the effect of post-processing procedure performed on the ultrasonic images in practicing the method as described below.
Figure 4B:
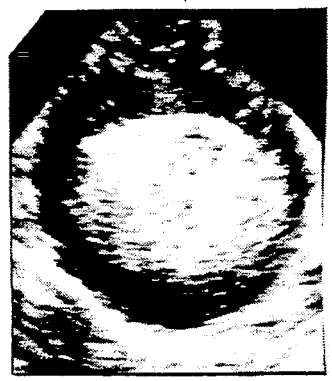
Figure 4C:
Figure 4D:
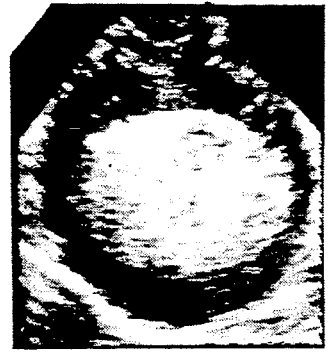

It is believed that the invention will be better understood by discussing the basic concepts involved in the present invention. To facilitate the understanding of these basic concepts, we set forth below definitions of the abbreviations used in the equations appearing in this discussion.

DEFINITIONS

V—volume of a sample of myocardial tissue;
f—fraction of volume V occupied by capillary bed;
$<t>$—mean transit time of microbubbles through the tissue sample;
$c_s(t)$—concentration of bubbles in the capillaries in tissue sample;
$c_p(t)$—concentration of bubbles in a homogeneous blood pool upstream the tissue sample;
$I_s(t)$—ultrasonic reflection intensity from the tissue sample produced by microbubbles;
$\tilde{I}_s(\omega)$—Fourier transform of $I_s(t)$;
$I_p(t)$—reflection intensity from the blood pool produced by the bubbles;
$\tilde{I}_p(\omega)$—Fourier transform of $I_p(t)$;
$R_s(t)$—echocardiographic impulse response function of the tissue sample;
$\tilde{R}_s(\omega)$—transfer function of the tissue sample (Fourier transform of $R_s(t)$);
$M_s(t)$—total number of bubbles in volume V of the tissue sample;
$M_p(t)$—total number of bubbles in volume V of blood in the pool;
J—total blood flow through the tissue sample (in ml/min);
j—perfusion in the sample tissue (in ml/gr/min);
τ—minimal time of passage from the pool to the tissue sample;

INDICATOR DILUTION PRINCIPLES

As indicated above, the method of the present invention is based on the application of the basic principles of indicator dilution theory to flow dynamics in the microvasculature of a selected area of myocardial tissue, as assessed by contrast enhanced echocardiography. According to this theory, the amount of fluid flowing through a hydrodynamic system with a known volume in unit time (i.e., the flow), may be evaluated by introducing into the system small inert tracer particles not affecting the behavior of the system, that can be traced by appropriate means.

In a multiple branching system with a single input and a single output, each entering tracer particle leaves with a specific time delay. Measuring the time of transit of many particles may yield a mean time of transit of the tracer through the given system. This time may be easily evaluated when a certain amount of tracer is injected instantaneously at the system input and its concentration $c_{out}(t)$ is continuously monitored at the system output, using the following expression:

$$<t> = \frac{\int_0^\infty t c_{out}(t)dt}{\int_0^\infty c_{out}(t)dt} ; \qquad (1)$$

Since the dynamics of the ideal tracer must be identical to that of the fluid in the system, the mean transit time of the tracer particles represents the time for the entire volume to be replaced by the inflow of fresh fluid. Therefore, provided that the volume of fluid in the system, fV, and the mean of transit time, $<t>$, are known, the flow may be obtained by:

$$J = \frac{fV}{<t>} . \qquad (2)$$

MEAN TRANSIT TIME EVALUATION

The above approach to the evaluation of the mean transit time is restricted to a system characterized by a single input and a single output, as $c_{out}(t)$ must be monitored at the system output. In a system with a single input and more than one output, tracer concentration as a function of time may vary significantly between the different outputs, due to varying pathways and varying degrees of mixing.

Since a sample of myocardial tissue cannot be regarded as single output model, the simultaneous measurement of tracer concentration at all output points is required. However, a nearly linear relation between the ultrasonic echo intensity and the concentration of microbubbles was shown to be true in an appropriate range of concentrations. The validity of this basic assumption is extended to a broader range of concentrations by subjecting the images to a path-dependent recompensation procedure described further on. Thus, the requirement of multiple point measurement of tracer concentration is satisfied by simultaneously measuring echo intensity at all points of the sample tissue. Thus, considering mean echo intensity in the tissue, $I_s(t)$, rather than tracer concentration $c_{out}(t)$, we may noninvasively obtain a quantitative estimate of the mean transit time of a particle through the sample tissue by:

$$<t> = \frac{\int_0^\infty t I_s(t) dt}{\int_0^\infty I_s(t) dt}. \tag{3}$$

All of the above assumes an instantaneous bolus injection at the system input. However, the coronary circulation does not fully comply with this assumption, since even a direct intracoronary injection of contrast medium does not deliver the entire amount of tracer as a short bolus into a region of interest. Since the sample is in part supplied by blood entering from the capillary bed of the adjacent regions, each having its specific distribution of transit times, the inflow function of tracer is subject to delay, widening and damping. It becomes even more widened and damped, the more distant the sample is form the site of injection. This effect will be even more pronounced in case of a peripheral intravenous injection, because microbubbles introduced intravenously must traverse the lungs before entering the left heart, obviously involving different pathways and different arrival times.

The echo-intensity $I_s(t)$ measured in the tissue sample depends in turn on the configuration of the tracer inflow, so that a prolonged inflow will produce an essentially different, widened and damped $I_s(t)$. Therefore, the evaluation of the mean transit time according to eq. (3) would result in an overestimation of the mean transit time. This difficulty may however be resolved by using the following approach.

We define $I_0(t)$ as the intensity measured at the port of entry to the tissue sample. Accordingly, $I_s(t)$ may be considered as a convolution of $I_0(t)$, with an appropriate response function $R_s(t)$ characteristic for the specific sample and independent of the tracer inflow configuration:

$$I_s(t) = I_0(t) * R_s(t). \tag{4}$$

In case of an instantaneous injection of indicator directly at the input point, $I_0(t)$ may be idealized by a Dirac $\delta$-function, defined as follows:

$$\delta(t - t_0) = \begin{cases} \infty, & \text{for } t = t_0 \\ 0, & \text{for } t \neq t_0 \end{cases} \tag{5}$$

where $t_0$ is the instant of injection. The definition of the $\delta$-function also includes the constraint:

$$\int_{-\infty}^{\infty} \delta(t - t_0 - t') dt' = 1. \tag{6}$$

Assuming $t_0 = 0$, the convolution integral in eq. (4) may be rewritten and evaluated:

$$I_s(t) = \int_{-\infty}^{\infty} R_s(t') \delta(t - t') dt' = R_s(t). \tag{7}$$

Therefore, following an instantaneous injection, the response function $R_s(t)$ and $I_s(t)$ are in fact identical functions. For this reason, the response function is often referred to as the 'impulse response'. Thus, the mean transit time of the indicator particles may be generally evaluated for injection of any configuration by:

$$<t> = \frac{\int_0^\infty t R_s(t) dt}{\int_0^\infty R_s(t) dt}, \tag{8}$$

provided the response function $R_s(t)$ is known.

Theoretically, if $I_0(t)$ and $I_s(t)$ are known or measurable, $R_s(t)$ may be determined as follows. Applying a Fourier transform to both sides of eq. (4) and using the convolution theorem, we obtain the following:

$$\tilde{I}_s(\omega) = \tilde{I}_0(\omega) \tilde{R}_s(\omega), \tag{9}$$

where the twiddle indicates the Fourier transform of each function in the frequency domain. The transfer function is therefore given by:

$$\tilde{R}_s(\omega) = \frac{\tilde{I}_s(\omega)}{\tilde{I}_0(\omega)}, \tag{10}$$

and the impulse response is obtained by the inverse Fourier transform:

$$R_s(t) = FT^{-1}[\tilde{R}_s(\omega)]. \tag{11}$$

An approximate determination of the impulse response $R_s(t)$ is possible, since $I_s(t)$ is easily obtainable from the sample tissue, and $I_0(t)$ may be replaced (as a first approximation) by the intensity of the reflection from a homogeneous blood pool upstream the sample tissue, such as the aortic root or the left ventricle. Using this approximation requires additional correction for the time of passage from the pool to the entrance to the sample:

$$I_0(t) \approx I_p(t + \tau), \tag{12}$$

where the time delay $\tau$ can be estimated by measuring the time between contrast appearance in the pool and its appearance in the tissue sample.

Therefore, the mean transit time through the sample tissue may be approximately determined according to eq. (8).

BLOOD VOLUME EVALUATION

Blood volume in the microscopic blood vessels supplying the sample tissue may be as well evaluated by the analysis of the time dependence of echo intensities curves. The amount of tracer in volume V of blood in the pool, $M_p(t)$, may be expressed as:

$$M_p(t) = V c_p(t). \tag{13}$$

Similarly, the amount of tracer in the tissue sample, $M_s(t)$, may be expressed as the product of blood volume of the capillary bed of the sample tissue, fV, and the concentration of the tracer in the capillaries, $c_s(t)$:

$$M_s(t) = fV c_s(t). \tag{14}$$

Dividing eq. (13) by eq. (12) and integrating with respect to time we obtain:

$$\frac{\int_{-\infty}^{+\infty} M_S(t)dt}{\int_{-\infty}^{+\infty} M_p(t)dt} = f\left[\frac{\int_{-\infty}^{+\infty} c_S(t)dt}{\int_{-\infty}^{+\infty} c_p(t)dt}\right]. \quad (15)$$

It should be noted that tracer concentration $c_S(t)$ reaches its maximum value with some delay relative to the concentration in the pool, $c_p(t)$. Also, due to the different pathways used by the tracer particles in the sample tissue, certain mixing takes place. Thus, the maximal tracer concentration in the blood entering the sample tissue, $c_S(t)$, does not reach the same level as that in reference region, $c_p(t)$, although both regions are supplied from the same origin. However, the conservation of mass requires that:

$$\int_{-\infty}^{+\infty} c_S(t)dt = \int_{-\infty}^{+\infty} c_p(t)dt; \quad (16)$$

and therefore eq. (15) is immediately reduced to:

$$f = \frac{\int_{-\infty}^{+\infty} M_S(t)dt}{\int_{-\infty}^{+\infty} M_p(t)dt}. \quad (17)$$

The result of eq. (17) promises to provide an estimate of f. However, $M_S(t)$ and $M_p(t)$ are not directly measurable, and they must be replaced by the ultrasonic reflection intensities $I_S(t)$ and $I_p(t)$ as explained below.

We may assume a nearly linear relationship between tracer-produced intensity of the ultrasonic reflection from a certain region of interest and the amount of tracer per unit volume in that specific region of interest. This is a very crude assumption, as long as linear time gain, widely utilized in commercial equipment, is used to compensate for path effects on the intensity of the beam. However, the validity of the assumption may be improved by using path-dependent compensation for attenuation effects. Though several algorithms are known to produce such path-dependent compensation in the process of creating the images, none is routinely applied in clinics. We use an algorithm described further on to perform a post-processing digital recompensation of the echocardiographic images for path dependent attenuation.

Thus, reflection intensity from the pool, $I_p(t)$, may be expressed as:

$$I_p(t) = \zeta \frac{M_p(t)}{V};$$

or $$M_p(t) = \frac{VI_p(t)}{\zeta}. \quad (18)$$

Similarly, reflection intensity from the myocardial tissue sample, $I_S(t)$, may be expressed as:

$$I_S(t) = \zeta \frac{M_S(t)}{V};$$

or $$M_S(t) = \frac{VI_S(t)}{\zeta}. \quad (19)$$

Dividing eq. (19) by eq. (18) and integrating with respect to time, we obtain:

$$\frac{\int_{-\infty}^{+\infty} M_S(t)dt}{\int_{-\infty}^{+\infty} M_p(t)dt} = \frac{\int_{-\infty}^{+\infty} I_S(t)dt}{\int_{-\infty}^{+\infty} I_p(t)dt}. \quad (20)$$

Equating (20) with (17) we obtain:

$$f = \frac{\int_{-\infty}^{+\infty} I_S(t)dt}{\int_{-\infty}^{+\infty} I_p(t)dt}. \quad (21)$$

Therefore, measuring tracer-produced echo intensities in the myocardial tissue sample and the left ventricle or the aortic root, allows to obtain an estimate of the fraction of volume of the sample occupied by capillary bed.

REGIONAL PERFUSION EVALUATION

According to eq. (2), knowing the blood volume fV contained in the selected region of the myocardial tissue (in ml) and the mean transition time $<t>$ of the tracer (in min), we may obtain regional blood flow in ml/min by eq. (2). In order to obtain regional perfusion in ml/100 g/min, the result of eq. (2) must be divided by tissue mass (in gram) and multiplied by 100. Assuming that characteristic density of mass of soft living tissue may well be approximated to 1 g/cm³, this yields the following:

$$j = \frac{fV}{<t>} \cdot \frac{100}{V} = \frac{100f}{<t>} \quad (22)$$

Substituting eq. (20) for f, we obtain an estimate for myocardial regional perfusion in units of ml/100 g/min:

$$\boxed{j = \frac{\int_{-\infty}^{+\infty} I_S(t)dt}{\int_{-\infty}^{+\infty} I_p(t)dt} \cdot \frac{100}{<t>}} \quad (23)$$

DIGITAL PATH-DEPENDENT RECOMPENSATION OF CONTRAST ENHANCED ECHOCARDIOGRAPHIC IMAGES

The linear compensations for propagation attenuation, commonly utilized in the two dimensional ultrasonographic imaging, is based on the assumption of uniform scattering and energy absorption in all biological materials. This approximation produces images, with regional video intensity directly affected by the scattering and absorption properties of the tissues more proximal to the transducer. Thus, structures with reflecting properties above the average, produce areas of acoustic shading at the underlying tissues and organs, for which the standard correction is not sufficient. Similar effect may be produced highly absorbing media, such as microscopic air bubbles used for contrast enhancement. On the other hand, over-correction caused by standard time-gain compensation in highly homogeneous tissues, such as the ventricular cavity or the gallbladder, results in a distal sonic enhancement of the underlying tissues.

Though the intensity variations caused by the above compensation methods may be very large, they do not necessarily impede the interpretation of the ultrasonographic images by visual examination, due to the special properties of human visual perception. An experienced diagnostician may base on these images his complex but reliable diagnostic distinctions.

However, the linear time gain compensation for attenuation is especially inadequate in contrast echocardiographic studies attempting to quantitate the contrast enhancement of myocardial tissue, based on the requirement that the regional variations in video intensity of a region of interest be entirely dependent on the presence of contrast material in that specific region, and not the surrounding tissues. Contrast solution injected into blood circulation does not reach selectively the region of interest, thus causing gradual contrast enhancement in the different regions of the image, and changing the attenuation conditions to which the beam is subject first. Therefore, a vigorous effort to produce recompensation regarding the dynamic changes in attenuation properties of the different structures induced by contrast enhancement, is essential for the reliable quantitative analysis of contrast appearance and washout.

The following algorithm is used in our method for recompensating the ultrasonographic video intensity for the non-uniform scattering and absorption. The algorithm is based on a robust model of beam attenuation by scattering and the comparison of the corrections necessary with and without the assumption of uniform scattering. It is implemented in an adaptive path-dependent computer post-processing procedure that accounts for the variable reflections from the different points along the acoustic beam.

DEFINITIONS $I_0(z)$—the intensity of the ultrasonic wave incident at depth z;
$I_0(O)$—the intensity of the ultrasonic wave sent by the transducer;
$I_s(z)$—the intensity of the scattered wave from a target volume at depth z;
$I_t(z)$—the intensity of the wave transmitted through the target volume at depth z;
$I_a(z)$—the intensity of the wave absorbed by the target volume at depth z;
$I_r(z)$—the intensity received by the transducer from the depth z;
$\mu(z)$—intensity attenuation coefficient at depth z;
$\alpha(z)$—intensity reflection coefficient at depth z;
$\alpha_a(z)$—intensity absorption coefficient at depth z;
$c^{(i)}(z)$—first order correction factor;
$c^{(ii)}(z)$—second order correction factor;
$v(\vec{r})$—video intensity value assigned to a picture element at vector coordinates $\vec{r}$ of the two dimensional echo image;
G—gain or scaling factor between reflection coefficient $\alpha_r(z)$ and video intensity $v(\vec{r})$.

We discretize the tissues traversed by the ultrasonic wave to finite elements corresponding to the pixels of the ultrasonographic image, along radial paths starting at the location of the transducer. These small elements are simplified into small reflectors normal to the direction of the incident wave, however large enough relative to the wavelength in order to produce specular reflection at the backward direction. The reflections from different depths are received by the transducer and processed to produce ultrasonographic images with varying regional video intensity patterns, thus allowing to visualize human anatomy.

We may consider an ultrasonic wave incident at an interface between two different tissues within a target volume located at depth z. A part of the incident intensity is reflected by the interface due to the difference in the characteristic impedances of the two media. The intensity of the transmitted wave may be written as:

$$I_t(z) = I_0(z) - (I_r(z) + I_a(z)), \qquad (24)$$

and the reflected part of the incident intensity may be expressed as:

$$I_r(z) = \alpha_r(z) I_0(z). \qquad (25)$$

Therefore, we may write:

$$I_t(z) = I_0(z)[1 - (\alpha_r(z) + \alpha_a(z))] = I_0(z)[1 - \mu(z)]. \qquad (26)$$

ZERO ORDER APPROXIMATION

Assuming that no significant attenuation takes place due to the reflections and absorption by the elements proximal to the target volume, one could conclude that the incident beam intensity is independent of the depth:

$$I_0(z) = \text{const} = I_0(0), \qquad (27)$$

and the reflection from the target volume is:

$$I_r(z) = \alpha_r(z) I_0(0). \qquad (28)$$

In this case, the zero order approximation for the reflection coefficients of a series of successive volume elements would be:

$$\alpha_r^{(0)}(z) = \frac{I_r(z)}{I_0(0)}, \qquad (29)$$

or $$\alpha_r^{(0)}(z) = \frac{I_r(z)}{I_0(0)}. \qquad (30)$$

since the backscattered wave is not subject to attenuation as well.

FIRST ORDER APPROXIMATION

Assuming that the reflection and absorption properties of all elements along the path leading to the target volume are approximately the same, we may simplify the problem of estimating the attenuation coefficients at different depths by introducing a mean attenuation coefficient along the path:

$$\overline{\mu}(z) = \frac{1}{z}\int_0^z \mu(z')dz'. \qquad (31)$$

The problem may be further simplified by saying that $\overline{\mu}(z)$ is fairly similar for the relevant biological materials $\overline{\mu}(z) \simeq \overline{\mu}$. This kind of approximation is widely used by commercial ultrasonic imaging equipment, and the value of $\overline{\mu}$ can be found in the literature. This mean value may be used for estimating the reflection intensity from the target volume in the following recursive manner, based on eqs. (24) and (25):

$$\begin{aligned}
I_r(z) &= a_r(z) I_0(z) = \\
&= a_r(z) I_r(z - \Delta z) = \\
&= a_r(z)(1 - \overline{\mu}) I_0(z - \Delta z) = \\
&= a_r(z)(1 - \overline{\mu})^2 I_0(z - 2\Delta z) = \\
&= \ldots = a_r(z)(1 - \overline{\mu})^N I_0(0),
\end{aligned} \qquad (32)$$

where $\Delta z$ is a discretization step between two successive reflectors, and N is the number of the reflectors along the radial path leading to the target volume. On its path from the target volume back to the transducer, the reflected wave is subject to the same attenuation as the original wave before reaching depth z. Thus, for the intensity detected by the transducer after the round trip to the target, is a result of a repeated attenuation by each of the proximal elements. Therefore, the attenuation factor should be squared, and we obtain:

$$I_r(z) = a_r(z)(1 - \overline{\mu})^{2N} I_0(0). \qquad (33)$$

Finally, the first order approximation for the reflection coefficients as a function of depth is:

$$a_r^{(i)}(z) = \frac{I_r(z)}{I_0(0)} \cdot \frac{1}{(1 - \overline{\mu})^{2N}}, \qquad (34)$$

differing from that in eq. (30) by a first order correction factor $c^{(i)}(z)$:

$$c^{(i)}(z) = \frac{1}{(1 - \overline{\mu})^{2N}}. \qquad (35)$$

SECOND ORDER APPROXIMATION

Likewise, we may derive the following expression for the reflected intensity from the target volume, fully taking into account the local attenuation of each element along the path:

$$\begin{aligned}
I_r(z) &= a_r(z) I_0(z) = \\
&= a_r(z) I_r(z - \Delta z) = \\
&= a_r(z)[1 - \mu(z - \Delta z)] I_0(z - \Delta z) = \\
&= a_r(z)[1 - \mu(z - \Delta z)] I_r(z - 2\Delta z) = \\
&= a_r(z)[1 - \mu(z - \Delta z)] \\
&\quad [1 - \mu(z - 2\Delta z)] I_0(z - 2\Delta z) = \\
&= \ldots = a_r(z)\left(\prod_{n=1}^{N}[1 - \mu(z - n\Delta z)]\right) I_0(0).
\end{aligned} \qquad (36)$$

The effect of the round trip of the intensity of the ultrasonic wave is similar to that in the first order approximation (see eq. (33)):

$$I_r(z) = a_r(z)\left(\prod_{n=1}^{N}[1 - \mu(z - n\Delta z)]^2\right) I_0(0). \qquad (37)$$

Therefore, the second order approximation for the reflection coefficients as a function of depth will be:

$$a_r^{(ii)}(z) = \frac{I_r(z)}{I_0(0)} \cdot \frac{1}{\prod_{n=1}^{N}[1 - \mu(z - n\Delta z)]^2}, \qquad (38)$$

or changing the direction of counting of elements on the same path:

$$a_r^{(ii)}(z) = \frac{I_r(z)}{I_0(0)} \cdot \frac{1}{\prod_{n=0}^{N-1}[1 - \mu(n\Delta z)]^2}. \qquad (39)$$

This forward direction allows the evaluation of the reflection coefficients starting at $n=0$ where no correction is necessary, and forth to the target volume.

The second order correction factor $c^{(ii)}(z)$ is therefore given by:

$$c^{(ii)}(z) = \frac{1}{\prod_{n=0}^{N-1}[1 - \mu(n\Delta z)]^2}, \qquad (40)$$

RECOMPENSATION OF THE FIRST ORDER PATH DATA

Comparing eq. (34) with eq. (39), we can apply to data obtained with the above first order path-independent time-gain correction a simple recompensation procedure based on the second-order path-dependent approach:

$$a_r^{(ii)}(z) = a_r^{(i)}(z) \frac{c^{(ii)}(z)}{c^{(i)}(z)}, \qquad (41)$$

or in a more explicit recursive formulation:

$$a_r^{(ii)}(N\Delta z) = a_r^{(i)}(N\Delta z) \frac{(1 - \overline{\mu})^{2N}}{\prod_{n=0}^{N-1}[1 - \mu^{(ii)}(n\Delta z)]^2}. \qquad (42)$$

RECOMPENSATION OF THE TWO DIMENSIONAL ULTRASONOGRAPHIC IMAGES

The typical values of the reflection coefficients $a_r$ and absorption coefficients $\mu$ are in the range [0;1], whereas the gray scale values assigned to different picture elements in an eight-bit image processing system are integers between 0 and 255. Hence, in order to apply eq. (42) to the pixel values $v(\vec{r})$, they must be normalized by scaling factor G defined by:

$$v(\vec{r}) = G a_r(\vec{r}), \qquad (43)$$

where, $\vec{r}$ is the two dimensional vector coordinates of the target volume.

Since the intensity loss from the beam is partially due to scattering, we may write for the myocardial tissue that:

$$a_r(\vec{r}) = \lambda_m \mu(\vec{r}), \qquad (44)$$

where $\lambda_m$ is the fraction of the intensity loss in the myocardial tissue due to scattering.

Thus, based on eqs. (43) and (44), we obtain:

$$\mu(\vec{r}) = \frac{v(\vec{r})}{\lambda_m G}. \qquad (45)$$

Therefore, assuming that G and $\lambda_m$ are known, the recompensation of the gray scale pixel values will be performed along the radial paths in the following manner:

$$v^{(ii)}(N\Delta r, \theta) = v^{(i)}(N\Delta r, \theta) \frac{\left(1 - \frac{\bar{v}}{\lambda_m G}\right)^{2N}}{\prod_{n=0}^{N-1}\left(1 - \frac{v^{(ii)}(n\Delta r, \theta)}{\lambda_m G}\right)^2} \qquad (46)$$

where r and $\theta$ are the polar coordinates of the pixel with the transducer at the origin, and $\bar{v}$ is the mean video intensity of an image obtained prior to contrast injection, i.e. in the absence of air bubbles, whose acoustic properties differ significantly from those of biological materials.

Furthermore, eq. (43) implies that $$\bar{v} = G\bar{a}, \qquad (47)$$

which permits finding the value of G, necessary for the recompensation procedure according to eq. (46). The value of $\bar{\mu}$ for the myocardial tissue is $\bar{\mu} = 0.8$ per cm at the frequency of 5 MHz (which we used in the example presented below).

The value of $\lambda_m$ was found by optimizing the results of the recompensation procedure with respect to the video intensity of the different parts of the myocardium. In particular, nearly equal intensities were produced in all part of the myocardium, independently of their position relative to the left ventricular cavity, with $\lambda_m = 1/12$.

For the recompensation of the intensities within the left ventricular cavity during the passage of the contrast material, a different value of $\lambda$ was used: $\lambda_b$ in the range $\lambda_b = \lambda_m$ to $\lambda_b = 3.5 \lambda_m$, depending on the concentration of the contrast in the blood, i.e. proportional to the measured video intensity at each point of the left ventricular cavity.

EXAMPLE OF METHOD

The drawings illustrate one example of a method that was used in accordance with the present invention, and the results produced by such method.

The method was performed on a mongrel dog (24 kg, male) (box 2, FIG. 1), anesthetized with pentobarbital sodium (30 mg/kg body weight, intravenously). Blood pressure and ECG 4 were monitored continuously. The animal was intubated and respirated with a Bird Mark-8 apparatus. Body temperature was kept constant by a heating lamp. A 5% dextrose-0.9% saline solution was infused at a constant rate during the entire experiment through a polyethylene catheter inserted in a femoral vein to sustain an open intravenous line. Sternotomy and pericardiotomy were carried out, and a pericardial cradle was established for suspension of the heart.

Injections of ultrasonic tracer 6 were introduced into the blood of the subject 2, which produced temporary enhancement of the video intensity in the echocardiographic image of the different parts of the heart. In this described method, the tracer was a commercial human albumin solution containing sonicated stable microscopic air bubbles (Albunex, Molecular Biosystems Co.).

The tracer was injected into the left atrium (which is upstream of the region of interest, and also upstream of a reference region specified within the left ventricular cavity). For each injection, a dose of 0.25 ml of Albunex, slightly hand-agitated prior to the injection, and 2.75 ml of 5% human Albumin, was manually introduced directly to the left atrium. The respiration was stopped for a short period of image acquistion (less than 1 min), in order to minimize cardiac translation due to respiratory chest movements.

The heart (including the region of interest in the heart muscle tissue and the reference region in the left ventricle) was subjected to ultrasonic imaging. In this specific example, imaging was performed using Aloka 870-SSD apparatus 12 with a 5 MHz phased-array transducer 8, fixed on the left ventricular epicardial surface of the heart with a flexible mechanical arm. Two-dimensional slice images 14 of the heart were obtained, in a short axis view at the mid-ventricular level. All time-gain compensation controls were set to their default position. The overall gain was set so as to produce a gray scale value close to maximum of the scale (255) at peak enhancement of the left ventricular cavity. These gain settings were kept constant throughout the entire experiment.

The video signals 14 representing these images could be continuously displayed (box 16) on a monitor screen 18. Images corresponding to end-diastole of the successive heart beats were selectively acquired by a memory buffer 22 of a frame grabber computer board 24, using ECG gating (box 20), and passed to the computer 24 for magnetic storage.

Seven injections were performed as following:
1-3 control aimed at examining the reproducibility of the measurement;
4 hyperemia (increased blood flow) caused by dipyridamole 0.5 mg/kg (intra-atrial);
5 control aimed to reassure normal flow following 15 min rest period;
6 anterior wall ischemia (insufficient blood supply) caused by mechanical occlusion of the left anterior descending coronary artery;
7 control aimed to reassure normal flow following 15 min reperfusion.

For each injection, 64 end-diastolic frames were stored, including 10 pre-injection frames, 5 to 10 frames during contrast injection, and about 40 additional subsequent frames.

FIGS. 3a–3d illustrate four examples of a short axis image obtained under control conditions:
a) prior to contrast injection;

b) immediately after contrast injection (notice the enhanced contrast of the left ventricular cavity);
c) about 5 heart beats later (notice that echo intensity of the myocardial tissue is slightly enhanced as compared with image (a));
d) following contrast washout.

The following image processing operations were facilitated by a post-processing image monitor 28. All images were subjected to the digital path-dependent recompensation for non- uniform attenuation. Each radial path, starting at the location of the transducer was independently corrected in each image according to the algorithm in the method.

FIGS. 4a–4d illustrate the effect of the recompensation procedure upon two different images:
a) obtained before contrast injection;
b) obtained during contrast enhancement of the left ventricle;
c) image (a) following recompensation;
d) image (b) following recompensation.

The recompensated images were further processed as follows to produce a quantitative measurement of the regional myocardial blood flow (box 26):

1. For each injection, a reference region circumscribing the left ventricular cavity, and 12 different regions of interest (about 2000 pixels each) within the heart muscle surrounding the ventricle, were selected using a moving cursor. The above 12 regions of interest were denoted by numbers 0 to 11 clockwise, starting with 0 at the area above the left ventricle.
2. The mean video intensity within each region of interest and the reference region was evaluated in each of the 64 consecutive images, thus providing curves representing regional echo intensity as a function of time (boxes 42a,42b).
3. The intensities obtained for the heartbeats prior to contrast injection were averaged to obtain background intensity (boxes 44a,44b). Each background value was then subtracted from the corresponding function, resulting in a curve representing regional intensity produced exclusively by the microbubbles (boxes 48a,48b).
4. The instances of contrast appearance in each region were marked, and the video-intensity curves were shifted to zero time accordingly.
5. In order to minimize a possible artifact produced by the fast Fourier transform applied to functions with uneven edges, the functions $I_s(t)$ and $I_p(t)$ were multiplied by the function (boxes 52a,52b):

$$S[n] = 1 - \frac{1}{1 + \left(\frac{n_f}{n}\right)^p}, \tag{49}$$

where $n_f$, the right edge point, is marked manually and p is set to 30. This stage of the analysis and the preceding background subtraction, resulted in equalized zero edges.

6. Then the curves are subjected to the following smoothing procedure (boxes 54a,54b):

$$I_s[n] = \tfrac{1}{4} I_s[n-1] + \tfrac{1}{2} I_s[n] + \tfrac{1}{4} I_s[n+1], \tag{50}$$
$$I_p[n] = \tfrac{1}{4} I_p[n-1] + \tfrac{1}{2} I_p[n] + \tfrac{1}{4} I_p[n+1]. \tag{51}$$

7. The functions $I_s(t)$ and $I_p(t)$ were both divided by the maximal value of $I_p(t)$, which results in values in the range [0;1] (boxes 56a,56b).
8. As a first step in the evaluation of the regional impulse response function, 64 zero values were added to the vectors representing the functions $I_s$ and $I_p$, producing 128 points long vectors necessary for the deconvolution computations. The expanded vectors were transformed from the time domain to the frequency domain using the fast Fourier transform (base 2, power 7) (boxes 58a,60a,58b, 60b). Since Fourier analysis assumes evenly spaced data, the vectors were supposed as a first approximation to be evenly spaced at 60/(mean heart rate) sec.
9. The complex values of the estimated transfer function were computed according to eq. (10) as following (box 62):

$$\widetilde{R}_s[m] = \frac{\overline{I_s[m]} \cdot |\overline{I_p[m]}|}{\overline{I_p[m]} \cdot (|\overline{I_p[m]}| + \psi)}. \tag{52}$$

This expression uses a simplified one-dimensional version of the Wiener filter, which is one of the most widely used deconvolution techniques in the practice of two dimensional image processing. It has been introduced here in order to minimize the artifact of 'the spectral contamination' of the response in the frequency domain due to the division by small, nearly zero values of $\overline{I}_p(\omega)$, mainly at high frequencies. The effects of different values of $\psi$ were studied and the optimum was found to be 0.02 for functions normalized as specified in step 7 above.

10. The transfer function is subjected to a smoothing procedure (box 64) similar to that applied to the original functions in step 6 above:

$$\widetilde{R}_s[m] = \tfrac{1}{4} \widetilde{R}_s[m-1] + \tfrac{1}{2} \widetilde{R}_s[m] + \tfrac{1}{4} \widetilde{R}_s[m+1], \tag{53}$$

11. The following frequency domain low pass filter (box 66) was applied to the transfer function:

$$\text{Filter}[m] = 1 - \frac{1}{1 + \left(\frac{m_f}{m}\right)^p}. \tag{54}$$

This filter is of the form of the function S[n] defined in eq. (15). The parameter $m_f$, the cutoff frequency, is related to the full width at half maximum (FWHM) of $I_p(t)$ according to the following empirical formula:

$$m_f = 11 + \frac{72}{FWHM}, \tag{55}$$

and p was set to 20.

12. The evaluated transfer function was subjected to an inverse fast Fourier transform (box 68), resulting in the time domain impulse response (box 70), according to eq. (11).
13. The evaluated impulse response was multiplied by S(t) function defined by eq. (45), where p was set to 20 and $n_f$=CT, the cutoff time, determined such as to retain 98% of the area under the curve representing $R_s(t)$, while the remaining 2% tail is neglected. The last points corresponding to this tail were set to zero by multiplication with S(t) (box 72).

14. The mean transit time of the contrast through each region of interest was evaluated according to eq. (8), using a simple rectangular approximation for numerical integration (box 74).
15. The integrals in eq. 21 were obtained by summing up the values of the background subtracted intensities in the region of interest and the reference region (box 76).
16. Regional perfusion was finally computed (box 78) according to eq. (23).

RESULTS

Figure 5:
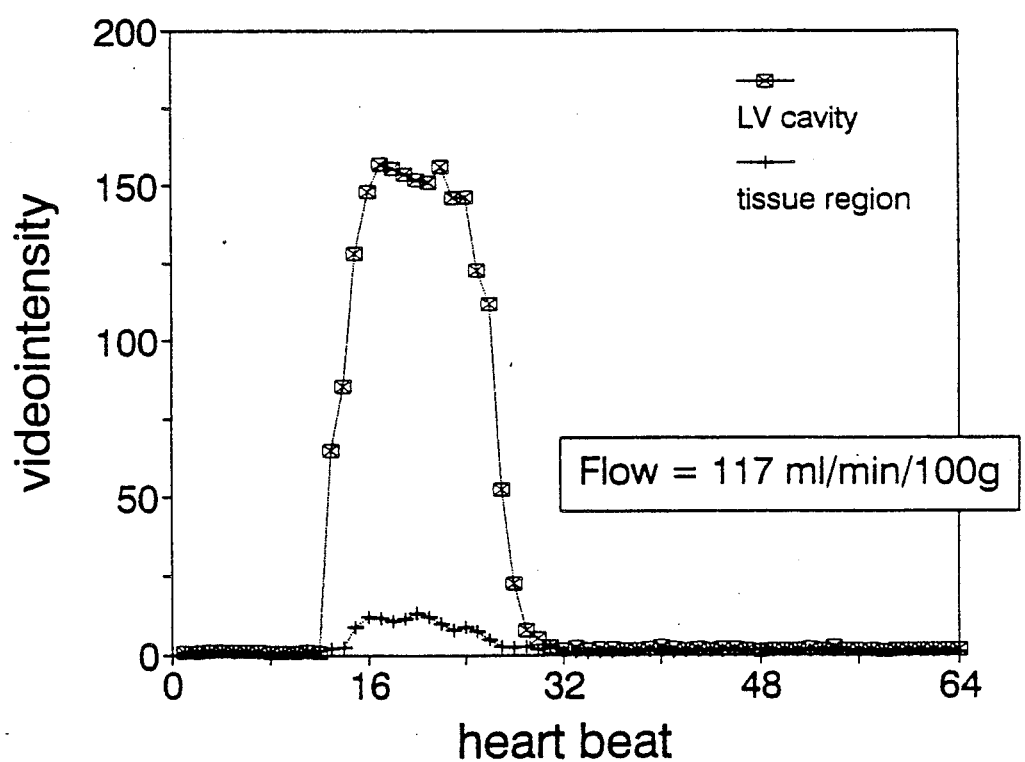
FIG. 5 illustrates a typical computer output of the numerical analysis performed during practicing the method in the example described below.

Regional myocardial blood flow was thus evaluated in each of the 12 selected regions of the myocardial tissue. FIG. 5 presents an example of computer output of the numerical analysis obtained for one region of interest. In addition to the computed flow, the evaluated response function is presented (solid line) and the mean transit time of the region of interest is displayed under the time axis. The reconvolved intensity is also displayed (dashed line) and may be compared with the experimental intensity in the, to appreciate the precision of the analysis.

The values of the regional blood flow measured under the different conditions (injections 1–7) were found to be in the physiological ranges likely to be observed in each case. The variations in the flow values in any region following any two different control injections did not exceed 20% of their mean value. The complete ligation of the coronary artery reduced the flow value measured in the regions originally supplied by the occluded artery to very low residual values, while dipyridamole injection resulted in significantly increased measured flow.

While the invention has been described with respect to one preferred embodiment, it will be appreciated that many variations, modifications and other applications of the invention may be made.

What is claimed is:

1. A method of measuring blood flow through the tissue in a region of interest, comprising the following steps:
   (a) injecting an ultrasonic tracer substance into the blood upstream of the region of interest and also upstream of a specified reference region;
   (b) subjecting the region of interest and the specified reference region to ultrasonic waves;
   (c) simultaneously detecting the echo intensity at the region of interest and the reference region at the same phase of a series of successive heartbeats, to produce echo intensity values as a function of time for the region of interest and for the reference region;
   (d) measuring the mean background value in each region before the injection, and subtracting the mean background values from the detected echo intensity values at both regions to produce a measurement of the tracer-produced echo intensity functions;
   (e) utilizing said latter echo intensity functions to compute: (i) the mean transit time of the tracer through the region of interest; and (ii) the blood volume within the region of interest;
   (f) dividing the results of (e) (ii) by (e) (i) to produce a quantitative measurement of the blood flow through the tissue in the region of interest.

2. The method according to claim 1, wherein: the mean transit time of the tracer through the region of interest in step (e) (i) is computed by:
   (a) transforming the tracer-produced echo intensity functions in each region from the time domain to the frequency domain to produce a frequency domain intensity function for each region;
   (b) dividing the frequency domain intensity function in the region of interest by the frequency domain intensity function in the reference region to produce the transfer function of the tissue in the region of interest;
   (c) transforming the transfer function of the region of interest from the frequency domain to the time domain to produce the response function of the tissue in the region of interest;
   (d) and utilizing the latter response function to compute the mean transit time of the tracer through the tissue in the region of interest.

3. The method according to claim 1, wherein the blood volume within the region of interest in step (e) (ii) is computed by:
   (a) integrating with respect to time the tracer-produced echo intensity functions in the region of interest and in the reference region; and
   (b) dividing the former by the latter to produce a measurement of the fractional blood volume within the tissue in the region of interest, which when divided by the mean transit time, produces a quantitative measurement of the blood flow through the tissue per unit mass of the tissue (in ml/gr/min or other equivalent units).

4. The method according to claim 1, wherein said tracer substance is a solution containing microscopic particles, about the size of the red blood cells, capable of enhancing the intensity of the ultrasonic reflection.

5. The method according to claim 1, wherein in step (b), the region of interest and the specified reference region, are subjected to the two-dimensional ultrasonic imaging, and the acquired images are processed to produce a regional video intensity independent of tracer concentration in the surrounding regions.

6. The method according to claim 5, wherein the acquired images are processed to produce a regional video intensity independent of tracer concentration in the surrounding regions by subjecting said acquired images to digital path dependent time-gain recompensation.

7. A method of measuring blood flow through the tissue in a region of interest, comprising the steps:
   (a) injecting an ultrasonic tracer substance into the blood upstream of the region of interest and also upstream of a specified reference region;
   (b) subjecting the region of interest and the specified reference region to two-dimensional ultrasonic imaging, and processing the acquired images to produce a regional video intensity independent of tracer concentration in the surrounding region;
   (c) simultaneously detecting the echo intensity at the region of interest and the reference region at the same phase of a series of successive heartbeats, to produce echo intensity values as a function of time for the region of interest and for the reference region;

(d) measuring the mean background value in each region before the injection, and subtracting the mean background values from the detected echo intensity values at both regions to produce a measurement of the tracer-produced echo intensity functions;

(e) utilizing said measurement to compute: (i) the mean transit time of the tracer through the region of interest; and (ii) the blood volume within the region of interest;

(f) dividing the results of (e) (ii) by (e) (i) to produce a quantitative measurement of the blood flow through the tissue in the region of interest.

8. The method according to claim 7, wherein: the mean transit time of the tracer through the region of interest n step (e) (i) is computed by:
   (a) transforming the tracer-produced echo intensity functions in each region from the time domain to the frequency domain to produce a frequency domain intensity function for each region;
   (b) dividing the frequency domain intensity function in the region of interest by the frequency domain intensity function in the reference region to produce the transfer function of the tissue in the region of interest;
   (c) transforming the transfer function of the region of interest from the frequency domain to the time domain to produce the response function of the tissue in the region of interest;
   (d) and utilizing the latter response function to compute the mean transit time of the tracer through the tissue in the region of interest.

9. The method according to claim 8, wherein the blood volume within the region of interest in step (e) (ii) is computed by:
   (a) integrating with respect to time the tracer-produced echo intensity functions in the region of interest and in the reference region; and
   (b) dividing the former by the latter to produce a measurement of the fractional blood volume within the tissue in the region of interest, which, when divided by the mean transit time, produces a quantitative measurement of the blood flow through the tissue per unit mass of the tissue (in ml/gr/min or other equivalent units).

10. The method according to claim 7, wherein said tracer substance is a solution containing microscopic particles, about the size of the red blood cells, capable of enhancing the intensity of the ultrasonic reflection.

* * * * *

UNITED STATES PATENT AND TRADEMARK OFFICE
CERTIFICATE OF CORRECTION

PATENT NO. : 5,135,000
DATED : August 4, 1992
INVENTOR(S) : Akselrod et al.

It is certified that error appears in the above-identified patent and that said Letters Patent is hereby corrected as shown below:

On the title page, Item [73]: Inventor "Raizot" should read:
--Ramot--.

Signed and Sealed this

Twenty-fifth Day of January, 1994

Attest:

BRUCE LEHMAN

*Attesting Officer*  *Commissioner of Patents and Trademarks*